US00PP31508P2

(12) United States Plant Patent
Hofmann

(10) Patent No.: US PP31,508 P2
(45) Date of Patent: Mar. 3, 2020

(54) ***MANDEVILLA* PLANT NAMED 'INMANBOCLP'**

(50) Latin Name: *Mandevilla sanderi*
Varietal Denomination: Inmanboclp

(71) Applicant: Birgit Hofmann, Rudesheim am Rhein (DE)

(72) Inventor: Birgit Hofmann, Rudesheim am Rhein (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 0 days.

(21) Appl. No.: 16/350,760

(22) Filed: Dec. 31, 2018

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232, 226
CPC ... A01H 5/02; A01H 5/00; A01H 5/12; A01H 6/088; A01H 6/08
See application file for complete search history.

*Primary Examiner* — June Hwu
(74) *Attorney, Agent, or Firm* — C. A. Whealy

(57) ABSTRACT

A new and distinct cultivar of *Mandevilla* plant named 'Inmanboclp', characterized by its compact, upright and vining plant habit; moderately vigorous growth habit; freely branching habit; moderately glossy dark green-colored leaves; freely flowering habit; light red purple-colored flowers with darker red purple-colored venation and yellow orange-colored centers; and relative tolerance to low temperatures.

2 Drawing Sheets

Botanical designation: *Mandevilla sanderi.*
Cultivar denomination: 'INMANBOCLP'.

CROSS-REFERENCED TO CLOSELY-RELATED APPLICATIONS

Title: *Mandevilla* Plant Named 'Inmanbochp'
Applicant: Birgit Hofmann
Filed: Concurrently with this application

BACKGROUND OF THE INVENTION

The present invention relates to a new and distinct cultivar of *Mandevilla* plant, botanically known as *Mandevilla sanderi* and hereinafter referred to by the name 'Inmanboclp'.

The new *Mandevilla* plant is a product of a planned breeding program conducted by the Inventor in Johannesburg, South Africa and Heidesheim, Germany. The objective of the breeding program is to create new freely branching *Mandevilla* plants that flower freely and have attractive flowers that resist fading and sun scald.

The new *Mandevilla* plant is a naturally-occurring whole plant mutation of *Mandevilla sanderi* 'Inmanbocre'. The new *Mandevilla* plant was discovered and selected by the Inventor as a single flowering plant from within a population of plants of 'Inmanbocre' in a controlled greenhouse environment in Heidesheim, Germany in June, 2017.

Asexual reproduction of the new *Mandevilla* plant by vegetative cuttings in a controlled greenhouse environment in Heidesheim, Germany since June, 2017 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inmanboclp'. These characteristics in combination distinguish 'Inmanboclp' as a new and distinct *Mandevilla* plant:

1. Compact, upright and vining plant habit.
2. Moderately vigorous growth habit.
3. Freely branching habit.
4. Moderately glossy dark green-colored leaves.
5. Freely flowering habit.
6. Light red purple-colored flowers with darker red purple-colored venation and yellow orange-colored centers.
7. Relatively tolerant to low temperatures.

Plants of the new *Mandevilla* can be compared to plants of the mutation parent, 'Inmanbocre'. Plants of the new *Mandevilla* differ primarily from plants of 'Inmanbocre' in flower color as plants of the new *Mandevilla* have light red purple-colored flowers with darker red purple-colored venation and yellow orange-colored centers whereas plants of 'Inmanbocre' have deep red-colored flowers.

Plants of the new *Mandevilla* can be compared to plants of *Mandevilla sanderi* 'Inmanbochp', disclosed in a U.S. Plant patent application Ser. No. 16/350,761 filed concurrently. Plants of the new *Mandevilla* differ primarily from plants of 'Inmanbochp' in flower color as plants of the new *Mandevilla* have light red purple-colored flowers with darker red purple-colored venation and yellow orange-colored centers whereas plants of 'Imnanbochp' have red-colored flowers with yellow orange-colored centers.

Plants of the new *Mandevilla* can also be compared to plants of *Mandevilla hybrida* 'Sunmandecripi', disclosed in U.S. Plant Pat. No. 18,578. In side-by-side comparisons plants of the new *Mandevilla* differ primarily from plants 'Sunmandecripi' in the following characteristics:

1. Plants of the new *Mandevilla* are smaller than plants of 'Sunmandecripi'.
2. Plants of the new *Mandevilla* have larger flowers than plants of 'Sunmandecripi'.
3. Plants of the new *Mandevilla* have light red purple-colored flowers with darker red purple-colored venation and yellow orange-colored centers whereas plants of ' Sunmandecripi' have darker red purple-colored flowers with orange-colored centers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Inmanboclp' grown in a container.

The photograph on the second sheet is a close-up view of a typical flowering plant of 'Inmanboclp'.

DETAILED BOTANICAL DESCRIPTION

The aforementioned photographs and following observations, measurements and values describe plants grown during the spring and summer in 11-cm containers with wooden support frames in a glass-covered greenhouse in Heidesheim, Germany and under cultural practices typical of commercial *Mandevilla* production. During the production of the plants, day temperatures ranged from 20° C. to 40° C. and night temperatures ranged from 15° C. to 25° C. Plants were four months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'Inmanboclp'.

Parentage: Naturally-occurring whole plant mutation of *Mandevilla sanderi* 'Inmanbocre'.

Propagation:

*Type*.—By vegetative cuttings.

*Time to initiate roots, summer*.—About three weeks at temperatures ranging from 20° C. to 35° C.

*Time to initiate roots, winter*.—About three weeks at temperatures ranging from 20° C. to 25° C.

*Time to produce a rooted young plant, summer*.—About 20 to 25 days at temperatures ranging from 20° C. to 35° C.

*Time to produce a rooted young plant, winter*.—About 25 to 30 days at temperatures ranging from 20° C. to 25° C.

*Root description*.—Thick, fleshy; typically white in color, actual color of the roots is dependent on substrate composition, water quality, fertilizers, substrate temperature and physiological age of roots.

*Rooting habit*.—Low branching; medium density.

Plant description:

*Plant and growth habit*.—Upright and vining plant habit; roughly broadly obovate in overall shape; moderately vigorous growth habit and moderate growth rate.

*Plant height, soil level to top of foliar plane*.—About 27 cm.

*Plant height, soil level to top of floral plane*.—About 25.6 cm.

*Plant diameter* (*spread*).—About 32.1 cm.

*Lateral branch description*.—Branching habit: Freely branching habit, primary lateral branches each with about five secondary lateral branches. Length: About 17.7 cm. Diameter: About 2 mm. Internode length: About 3.8 cm. Aspect: Primary lateral branches, about 20° from vertical; secondary lateral branches, about 30° from primary branch axis. Strength: Strong. Texture and luster: Smooth, glabrous; glossy; becoming woody with development. Color, developing: Close to between 143B and 144A. Color, developed: Close to 144A; when woody, close to N199C.

Leaf description:

*Arrangement*.—Opposite, simple.

*Length*.—About 7 cm.

*Width*.—About 4.3 cm.

*Shape*.—Obovate to broadly elliptic.

*Apex*.—Short apiculate.

*Base*.—Truncate to obtuse.

*Margin*.—Entire; not undulate.

*Texture and luster, upper surface*.—Smooth, glabrous; moderately coriaceous; moderately glossy.

*Texture and luster, lower surface*.—Smooth, glabrous; moderately coriaceous; slightly glossy.

*Venation pattern*.—Pinnate.

*Color*.—Developing leaves, upper surface: Darker than 143A. Developing leaves, lower surface: Close to 146B. Full expanded leaves, upper surface: Close to between 139A and 147A; venation, close to 143B. Fully expanded leaves, lower surface: Close to 146B; venation, close to 145A.

*Petioles*.—Length: About 1.4 cm. Diameter: About 2 mm by 2.5 mm. Strength: Moderately strong. Texture and luster, upper surface: Smooth, glabrous; slightly glossy. Texture and luster, lower surface: Smooth, glabrous; moderately glossy. Color, upper surface: Close to 144A. Color, lower surface: Close to 144B.

Flower description:

*Flower type and flowering habit*.—Single salverform flowers arranged singly or in axillary cymes; flowers face mostly outwardly to somewhat upright; freely flowering habit with about two flowers per inflorescence and about 28 flower buds and open flowers developing per plant.

*Natural flowering season*.—Plants flower continuously from spring into the autumn in Germany; plants begin flowering about ten weeks after propagation.

*Flower longevity on the plant*.—Individual flowers last about ten days; flowers not persistent.

*Fragrance*.—None detected.

*Inflorescence height*.—About 8.9 cm.

*Inflorescence diameter*.—About 14.8 cm.

*Flower buds*.—Length: About 5.9 cm. Diameter: About 9 mm. Shape: Narrowly oblanceolate. Texture and luster: Smooth, glabrous; slightly glossy. Color: Distally, close to 56C to 56D; proximally, close to 145C; at the base, close to 145B.

*Flowers*.—Appearance: Flared trumpet, corolla fused and five-parted. Diameter: About 8.3 cm. Depth (length): About 7.2 cm. Throat diameter: About 1.3 cm. Tube length: About 4.8 cm. Tube diameter: Proximally, about 3.5 mm; distally, about 1.5 cm.

*Corolla*.—Quantity and arrangement: Five petals arranged in a single whorl; lower 57.5% portion of the petals are fused into a funnelform tube. Petal length: About 8.3 cm. Petal width: About 3 cm. Petal shape and appearance: Roughly spatulate. Petal apex: Apiculate. Petal margin: Entire; moderately undulate. Petal texture and luster, upper surface: Smooth, glabrous; moderately velvety; matte. Petal texture and luster, lower surface: Smooth, glabrous; slightly velvety; slightly glossy. Throat texture: Smooth, glabrous; moderately velvety. Tube texture: Smooth, glabrous; slightly velvety. Color: Petal, when opening, upper surface: Close to 69B; fading distally to close to 69A; at the throat, small spots, close to 61D. Petal, when opening, lower surface: Close to 69B; main vein, close to N155C. Petal, fully opened, upper surface: Close to 69B to 69C; at the throat, small spots, close to 58C; venation, close to 67C; color does not change with development. Petal, fully opened, lower surface: Close to 69B to 69C; main vein, close to 67D; color does not change with development. Throat: Close to 23A; proximally, close to 145C; venation, similar to lamina. Tube: Lighter than between 56D and 150D; proximally, close to 145A to 145B; venation, similar to lamina.

*Calyx*.—Quantity and arrangement: Five sepals arranged in a single whorl. Calyx length: About 8 mm. Calyx diameter: About 5 mm. Sepal length: About 7 mm. Sepal width: About 2 mm. Sepal shape: Lanceolate. Sepal apex: Narrowly acuminate. Sepal base: Broadly cuneate. Sepal margin: Entire. Sepal texture and luster, upper surface: Smooth, glabrous; moderately glossy. Sepal texture and luster, lower surface: Smooth, glabrous; slightly glossy. Sepal color: When developing, upper and lower surfaces: Close to 145B; tinged at the apex with close to 180C. Fully developed, upper and lower surfaces: Close to 145B; fading towards the base to close to 145A; tinged at the apex with close to 180C.

*Peduncles*.—Length: About 6.2 cm. Diameter: About 2 mm. Strength: Strong. Aspect: About 20° from lateral branch axis. Texture and luster: Smooth, glabrous; glossy. Color: Close to 144A.

*Pedicels*.—Length: About 1.5 cm. Diameter: About 2 mm. Strength: Strong. Aspect: About 25° from peduncle axis. Texture and luster: Smooth, glabrous; glossy. Color: Close to 145B.

*Reproductive organs*.—Stamens: Quantity and arrangement: Typically five; basifixed; anthers connivent. Filament length: About 1.5 mm. Filament color: Close to 151D. Anther shape: Narrowly oblong. Anther size: About 1 cm by 1.5 mm. Anther color: Close to 161B to 161C. Pollen amount: None observed. Pistils: Quantity: Typically one. Pistil length: About 2.3 cm. Style length: About 2 cm. Style color: Close to 145C. Stigma diameter: About 2 mm. Stigma shape: Club-shaped, pointed. Stigma color: Close to 147D. Ovary color: Close to 144B.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5° C. to about 40° C. and to be suitable for USDA Hardiness Zones 9 to 13.

It is claimed:

1. A new and distinct *Mandevilla* plant named 'Inmanboclp' as illustrated and described.

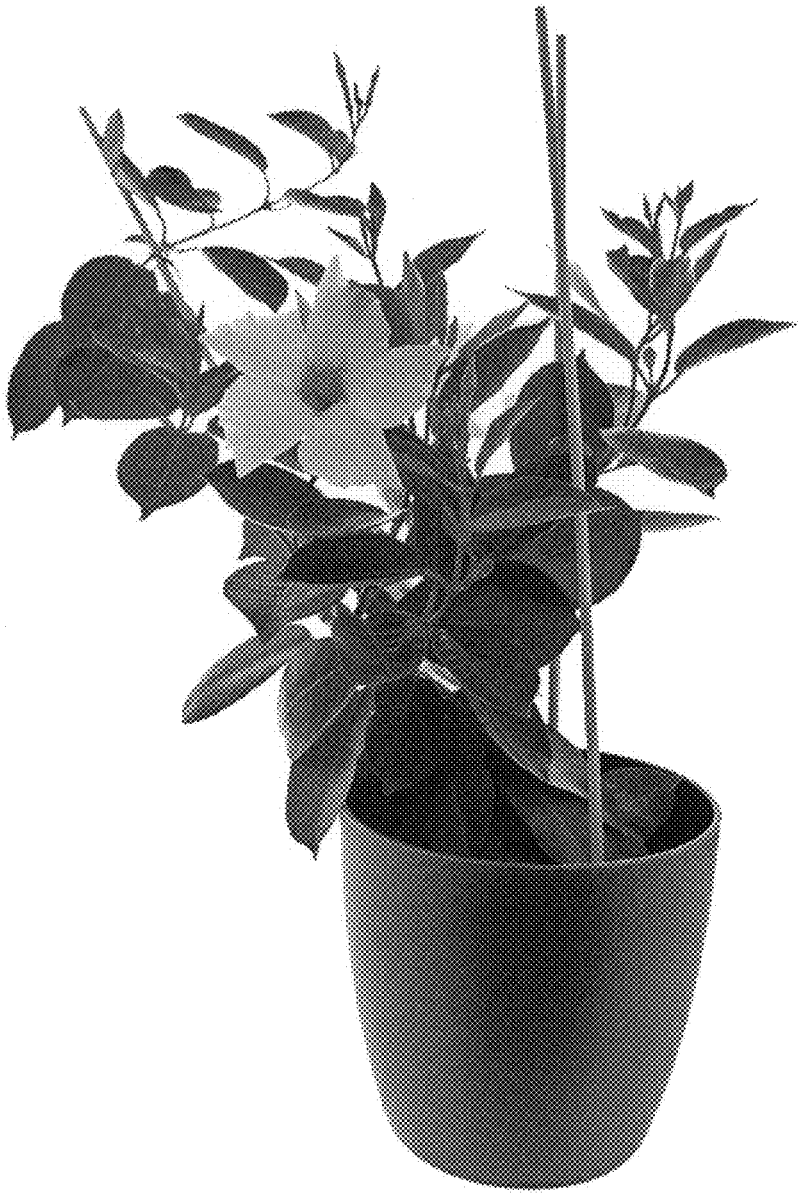

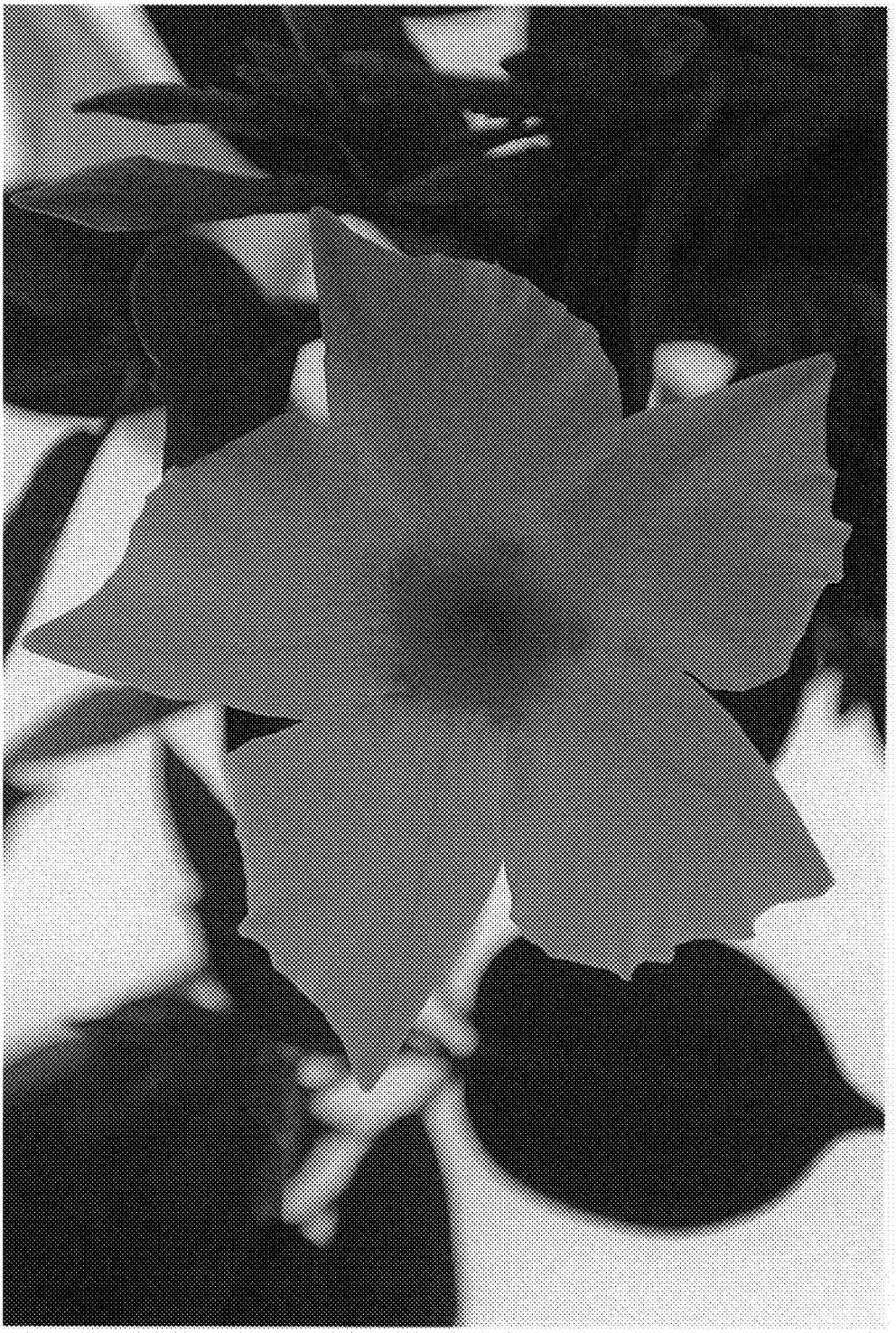

* * * * *